United States Patent [19]
Hosono et al.

[11] Patent Number: 6,068,970
[45] Date of Patent: *May 30, 2000

[54] METHOD OF PRESERVING CELLS USING CELL STORAGE BAG SYSTEM

[75] Inventors: Norio Hosono; Noboru Ishida, both of Shizuoka-ken, Japan

[73] Assignee: Terumo Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/900,916

[22] Filed: Jul. 28, 1997

Related U.S. Application Data

[63] Continuation of application No. 08/309,177, Sep. 20, 1994, abandoned.

[30] Foreign Application Priority Data

Sep. 20, 1993 [JP] Japan .................................. 5-256467

[51] Int. Cl.⁷ .............................. A01N 1/02; A61K 35/14
[52] U.S. Cl. ........................ 435/2; 435/304.1; 435/294.1; 435/307.1; 210/782; 604/410
[58] Field of Search ........................ 435/2, 288.1, 288.2, 435/294.1, 304.1, 304.2, 307.1, 308.1; 210/782, 512.1; 604/408, 410; 156/503

[56] References Cited

U.S. PATENT DOCUMENTS

| | | | |
|---|---|---|---|
| 3,951,148 | 4/1976 | Herb | 128/272 |
| 4,199,954 | 4/1980 | McGill | 62/62 |
| 4,267,269 | 5/1981 | Grode et al. | 435/2 |
| 4,369,779 | 1/1983 | Spencer | 128/213 |
| 4,412,835 | 11/1983 | Spencer | 604/29 |
| 4,443,215 | 4/1984 | Smith | 604/29 |
| 4,461,951 | 7/1984 | Luoma, II et al. | 219/497 |
| 4,476,631 | 10/1984 | Benin | 30/92 |
| 4,488,961 | 12/1984 | Spencer | 210/136 |
| 4,501,951 | 2/1985 | Benin et al. | 219/243 |
| 4,507,119 | 3/1985 | Spencer | 604/280 |
| 4,516,971 | 5/1985 | Spencer | 604/280 |
| 4,521,263 | 6/1985 | Benin et al. | 156/159 |
| 4,610,670 | 9/1986 | Spencer | 604/29 |
| 4,619,642 | 10/1986 | Spencer | 604/29 |
| 4,633,063 | 12/1986 | Willis | 219/243 |
| 4,647,756 | 3/1987 | Willis | 219/243 |
| 4,717,668 | 1/1988 | Keilman et al. | 435/304.1 |
| 4,786,286 | 11/1988 | Cerny et al. | 604/406 |
| 4,804,363 | 2/1989 | Valeri . | |
| 5,017,490 | 5/1991 | Taiariol et al. | 435/294.1 |
| 5,330,462 | 7/1994 | Nakamura | 604/410 |
| 5,399,268 | 3/1995 | Pall et al. | 210/757 |
| 5,417,681 | 5/1995 | Miyake et al. | 604/410 |

FOREIGN PATENT DOCUMENTS

| | | |
|---|---|---|
| 0 507 321 A1 | 10/1992 | European Pat. Off. . |
| 0 573 405 A1 | 12/1993 | European Pat. Off. . |
| 7-44947 | 5/1995 | Japan . |
| WO 86/04829 | 8/1986 | WIPO . |
| 90/04019 | 4/1990 | WIPO ................................ 435/308.1 |
| WO 91/01369 | 2/1991 | WIPO . |

OTHER PUBLICATIONS

EPO Official Action in corresponding EP application. Apr. 30, 1998.

*Primary Examiner*—William H. Beisner
*Attorney, Agent, or Firm*—Burns, Doane, Swecker & Mathis, LLP

[57] ABSTRACT

A cell storage bag system comprises a storage bag for containing cells to which at least one connecting tube having a closed end is connected, a reservoir container for containing an additive fluid to which a fluid supply tube having a closed end is connected, and a waste fluid container for receiving waste fluid to which a waste fluid tube having a closed end is connected. In the system, the at least one connecting tube is adapted to be connected to the fluid supply tube and/or said waste fluid tube by means of a tube connecting apparatus in a sterile manner, and when the connecting tube is connected to the fluid supply tube, the additive fluid is supplied to the reservoir bag through these connected tubes, and when the connecting tube is connected to the waste fluid tube, the waste fluid is collected from the storage bag through these connected tubes.

22 Claims, 9 Drawing Sheets

METHOD OF PRESERVING CELLS USING CELL STORAGE BAG SYSTEM

This application is a continuation of application Ser. No. 08/309,177, filed Sep. 20, 1994, now abandoned.

BACKGROUND OF THE INVENTION

1. Field of the Invention

The present invention relates to a cell storage bag system and a method of storing cells, and in particular relates to a cell storage bag system for storing cells such as red blood cells, white blood cells and blood platelets that have been separated from an extracted portion of blood, and also relates to a cell storage system for use in the cultivation of cells in a liquid medium.

2. Description of the Prior Art

In recent years, in order to prevent the spread of infectious diseases (for example, hepatitis, AIDS and the like) and the occurrence of immunological side effects as a result of blood transfusions between two different people having the same blood type, the practice of receiving a transfusion of one's own blood has gained attention. Among the methods for the transfusion of one's own blood, there is known a storage type transfusion. In the storage type transfusion, a blood reserve is established by removing blood from a patient (blood donor) prior to undergoing surgery and storing such removed blood in a blood bag which is itself then stored in a storage container for preserving the stored blood. Then, at the time the patient is to undergo surgery, the blood bag is removed from the storage container and the patient's blood stored therein is used to give the patient any needed blood transfusions during the course of the surgery.

At the time when such blood transfusions are being carried out, it is necessary to ensure that there is an adequate volume of blood available for transfusion, and this is done by carrying out one of several methods. In one method, this is accomplished by freezing the liquid blood stored in the blood bag. In another method the blood is maintained in liquid form in the blood bag, for example, employing the leap-frog method or the switch-bag method. In the switch-bag method, before the day of the surgery the blood that was previously stored is returned to the patient and then twice volume of the blood is once again extracted from the patient and stored. By employing these type of methods, it is possible to ensure a relatively large amount of fresh blood in a short period of time.

However, in order to employ the first method mentioned above, it is necessary to have the proper equipment for freezing the samples, and in addition to the maintenance that is required for such equipment, an inappropriate amount of time, labor and cost is required for freezing and thawing blood stored in the blood bags. As for the second method mentioned above using the switch-bag method, the frequent extraction and transfusion of blood results in a high physical burden on the patient. Further, if such methods are carried out by using the conventional blood bags, this method is unavoidably complicated due to the structure of the bags.

Moreover, with regards to the second method mentioned above, the effective storage period of the blood is rather short, and therefore there is a disadvantage in that it is sometimes not possible to store a sufficient amount of blood over such time period. Consequently, in order to overcome this disadvantage, in recent years much attention has been give to methods that make it possible to prolong storage times by exchanging preserving fluids.

This method involves the use of a multiple bag system in which a plurality of bags are joined by tubes. In this system, one bag is used for storing blood, and two other bags are divided into one bag that holds a fluid for preserving red blood cells and a second bag for holding waste fluids. During the storage of blood, supply of a nutrient source such as glucose and the like which is performed by supplying preserving fluid and removal of waste products such as lactic acid and the like contained in the fluid are performed in order within a closed system. This method, in comparison with the first and second methods mentioned above, makes it possible to greatly extend the length of time that the blood can be stored, and because this results in a lengthening of the interval between blood extractions, the burden on the patient is diminished. Therefore, this method is considered to have good future prospects.

However, in the method employing the multiple bags described above, because each bag is joined to each other, the preserving fluid and waste fluid must be stored together with the stored blood, which gives rise to the disadvantage that it becomes necessary for there to be a rather large storage space. Also, in order to separate out the preserving fluid in the blood bag in which waste products have been accumulated as waste fluid, the blood storage bag must centrifuged, and in this case it becomes necessary to carry out such centrifugal separation operation on all the bags of the multiple bag system. However, at the present time, the size of the centrifuging cup of centrifuging separators which are available does not allow the placement of five or more storage bags. Accordingly, multiple storage bag system must be limited to at most four bags, which places an upper limit on the amount of preserving fluids and waste fluids that can be contained by a multiple bag system.

Moreover, with the multiple bag system, when the blood storage bag is to be carried somewhere, all the other multiple number of bags that are joined therewith must also be carried together at the same time. Consequently, during transport of the multiple bag system, there is an increased likelihood of the bags being dropped or the bag system being damaged due to the connecting tubes being pulled. Furthermore, due to the unnecessary bags which are always attached thereto, when a fluid to be stored is being poured into the storage bag or when other storage operations are to be carried out, it is difficult to carry out such operations. Further, the time needed to complete such operations are increased, and this cumbersome arrangement also makes it easy for misoperations to occur.

Meanwhile, as general methods of cultivating cells, there is a method in which such cultivation is taken place by dispersing cells within a liquid medium stored inside a storage bag. When employing this type of cultivation method, in order to maintain the activity of the cells, it is necessary to change the liquid medium at regular intervals.

Up to now, liquid mediums have been changed by carrying out a method like the one that follows. Namely, the cell cultivating bag is placed on a clean bench or the like and a section of the tube connected therewith that is to be cut is sterilized with alcohol, and then that section of the tube is cut using a cutting tool such as a knife or scissors which have been heat sterilized. Then, the cell cultivating bag is lightly pressed to discharge the used up liquid medium out through the tube to be collected into a beaker or the like, and then the discharged liquid medium is collected. Next, fresh liquid medium contained in a cultivating medium preserving bag is transferred to the cell cultivating bag by inserting a needle, which is provided on the end of a liquid medium supply tube connected to the cultivating medium preserving bag, through a guiding portion of the cell cultivating bag and then passing the fresh liquid medium from the cultivating medium preserving bag through the liquid medium supply tube into the cell cultivating bag.

However, in the change method mentioned-above, because it is impossible to carry out exchange of the liquid mediums within a closed system, it is difficult to maintain sterile conditions. Consequently, at such times when the tube and the cutting tool are undergoing sterilization and when the liquid medium is being discharged, it is necessary to exercise extreme care in order to prevent bacterial contamination from occurring, and this labor intensive process results in a reduction in work efficiency.

SUMMARY OF THE INVENTION

It is an object of the present invention to provide a cell storage bag system and cell storage method which makes it possible to store cells for an extended length of time and to cultivate cells, and to maintain sterile conditions when adding an additive fluid and when discharging waste fluids. It is also an object of the present invention to provide a cell storage bag system and cell storage method that can be operated safely with ease. It is a further object of the present invention to provide a cell storage bag system having a cell storage bag having an economized storage space. It is yet another object of the present invention to provide a cell storage bag system which can be manufactured at a relatively low cost.

In order to achieve these objects, the cell storage bag system according to the present invention comprises a storage bag for containing cells, the storage bag including at least one connecting tube having a first end that communicates with the storage bag and a second end that is closed; a reservoir container for containing an additive fluid, the reservoir container including a fluid supply tube having a first end that communicates with the reservoir container and a second end that is closed; and a waste fluid container for receiving waste fluid, the waste fluid container including a waste fluid tube having a first end that communicates with the waste fluid container and a second end that is closed. In this system, the at least one connecting tube is adapted to be connected to the fluid supply tube and/or the waste fluid tube by means of a tube connecting apparatus in a sterile manner, and when the connecting tube is connected to the fluid supply tube, the additive fluid is supplied to the reservoir bag through these connected tubes, and when the connecting tube is connected to the waste fluid tube, the waste fluid is recovered from the storage bag through these connected tubes.

In the cell storage bag system described above, it is preferable that the reservoir container has a first connection tube for introducing the additive fluid and a second connection tube for discharging the waste fluid, in which the first connection tube is adapted to be connected to the fluid supply tube sterilely by means of the tube connecting apparatus, and the second connection tube is adapted to be connected to the waste fluid tube by means of the tube connecting apparatus. By doing so, the supply path of the additive fluid and the fluid path of the waste fluid can be differed with each other, so that no contamination will be caused between the waste fluid and new additive fluid, which results in improvement in operation efficiency for fluid replacements.

Alternatively, in order to achieve the above objects, the cell storage bag system according to the present invention comprises a storage bag for containing cells, the storage bag including a connecting tube having a first end that communicates with the storage bag and a second end that is closed; a reservoir container for containing an additive fluid, the reservoir container including a fluid supply tube having a first end that communicates with the reservoir container and a second end that is closed; a waste fluid container for receiving waste fluid, the waste fluid container including a waste fluid tube having a first end that communicates with the waste fluid container and a second end that is closed; and a connection tube having a first end that communicates with the fluid supply tube and the waste fluid tube and a second end that is closed. In this system, the connecting tube is adapted to be connected to the connection tube by means of a tube connecting apparatus in a sterile manner, in which supply of the additive fluid into the storage bag and/or recovery of the waste fluid from the storage bag is adapted to be carried out under the condition that the connecting tube is connected to the connection tube.

More preferably the cell storage bag system comprises a storage bag for containing cells, the storage bag including a connecting tube having a first end that communicates with the storage bag and a second end that is closed; a reservoir container for containing an additive fluid, the reservoir container including a fluid supply tube having a first end that communicates with the reservoir container and a second end that is closed and having an inner fluid passage; a waste fluid container for receiving waste fluid, the waste fluid container including a waste fluid tube having a first end that communicates with the waste fluid container and a second end that is closed and having an inner fluid passage; and a connection tube having a first end that communicates with the fluid supply tube and the waste fluid tube and a second end that is closed. In this system, the connecting tube is adapted to be connected to the connection tube by means of a tube connecting apparatus in a sterile manner, in which either of the inner fluid passages of the fluid supply tub and waste fluid tube is closed under the condition that the connecting tube is in connection with the connecting tube, so that the additive fluid is supplied to the reservoir bag through the fluid supply tube, the connection tube and the connecting tube when the inner fluid passage of the waste fluid tube is closed, and the waste fluid is recovered from the storage bag through the connecting tube, the connection tube, and the waste fluid tube when the inner fluid passage of the waste fluid tube is closed.

According to the systems described above, it is possible to perform discharge of the waste fluid from the storage bag and supply of the additive fluid to the storage bag only by one connecting operation between the connecting tube and the connection tube, which results in reducing the number of required tube connecting operations, thus leading to improvement in operation.

In these systems, it is preferable that the reservoir container comprises a fluid supply bag and the waste fluid container comprises a waste fluid bag.

Further, it is also preferable that the storage bag comprises a blood bag for storing blood or blood components, and the additive fluid is a preserving fluid for storing blood or blood components.

Furthermore, it is also preferable that the storage bag comprises a cell cultivating bag for cultivating cells, and the additive fluid is a cultivating medium for the cells.

Moreover, it is also preferable that the tube connecting apparatus comprises heat cutting means for heating tubes and thereby fusing and then cutting them, and a movable connecting means which moves the tubes so as to align a cut open end of one tube with a cut open end of the other tube and push the cut open ends together to form a connection therebetween.

Moreover, it is also preferable that each of the tubes is made of the same or similar type of thermoplastic resin, the movable connecting means comprises a pair of holders which hold the two tubes to be connected parallel with respect to each other and which are reciprocally movable in the direction of arrangement of the two tubes; and the heat cutting means comprises a heated cutting plate which is replaceably disposed between the holders and served to heat the tubes and thereby fuse and then cut the tubes.

By using the tube connecting apparatus, it is possible to connect tubes in a short time with easy operation. As a result, sterile conditions can be maintained during the tube connecting operations, and since the connected portions have sufficient strength, no breakage will be caused at the connected portions.

Further, in order to achieve the above objects, the cell storing method according to the present invention employs a cell storage bag system which comprises a storage bag for containing cells, the storage bag including at least one connecting tube having a first end that communicates with the storage bag and a second end that is closed, a reservoir container for supplying an additive fluid, the reservoir container including a fluid supply tube having a first end that communicates with the reservoir container and a second end that is closed, a waste fluid container for receiving waste fluid, the waste fluid container including a fluid waste tube having a first end that communicates with the fluid waste container and a second end that is closed, wherein the method is characterized by performing at lest one of the following steps during preservation of the cells: connecting the connecting tube with the waste fluid tube sterilely by using a tube connecting apparatus, and then transferring waste fluid from the storage bag to the waste fluid container through the connected tubes and collect it in the container; and connecting the connecting tube with the fluid supply tube sterilely by using the tube connecting apparatus, and then transferring the additive fluid from the reservoir container to the storage bag.

According to the method described above, it is possible to store the cells for long time and cultivate the cells. Further, supply of the additive fluid and discharge of the stored fluid can be performed sterilely with easy operation. Furthermore, no leakage of the fluid will be cause.

Alternatively, in order to achieve the above objects, the cell storing method according to the present invention may employs a cell storage bag system which comprises a storage bag for containing cells, the storage bag including a first connecting tube having a first end that is closed and a second end that is connected to the storage bag and a second connecting tube having a first end that is closed and a second end that is connected to the storage bag, a reservoir container for supplying an additive fluid, the reservoir container including a fluid supply tube having a first end that communicates with the reservoir container and a second end that is closed, a waste fluid container for receiving waste fluid, the waste fluid container including a fluid waste tube having a first end that communicates with the fluid waste container and a second end that is closed, wherein the method is characterized by performing the following steps in arbitrary order for arbitrary times during preservation of the cells: connecting the second connecting tube of the storage bag with the waste fluid tube sterilely by using a tube connecting apparatus, and then transferring waste fluid from the storage bag to the waste fluid container through the connected tubes to collect it in the container; and connecting the first connecting tube of the storage bag with the fluid supply tube sterilely by using the tube connecting apparatus, and then transferring the additive fluid from the reservoir container to the storage bag.

According to this method, since the additive fluid supply path is different from the fluid path for the waste fluid, no contamination will be caused between the waste fluid and new additive fluid, thus leading to improvement in fluid replacement efficiency.

Alternatively, in order to achieve the above objects, the cell storing method according to the present invention employs a cell storage bag system which comprises a storage bag for containing cells, the storage bag including a connecting tube having a first end that communicates with the storage bag and a second end that is closed, a reservoir container for supplying an additive fluid, the reservoir container including a fluid supply tube having a first end that communicates with the reservoir container and a second end that is closed, a waste fluid container for receiving waste fluid, the waste fluid container including a fluid waste tube having a first end that communicates with the fluid waste container and a second end that is closed, and a connection tube having a first end that is connected to both the fluid supply tube and waste fluid tube and a second end that is closed, wherein the method is characterized by performing the following steps in arbitrary order for arbitrary times during preservation of the cells: connecting the connecting tube of the storage bag with the connection tube sterilely by using a tube connecting apparatus, and then blocking an inner fluid path of the fluid supply tube, thereby transferring waste fluid from the storage bag to the waste fluid container by means of the connecting tube, connection tube and the waste fluid tube to collect it in the container; and blocking an inner fluid path of the waste fluid tube and opening the blocked inner fluid path of the fluid supply tube, and transferring the additive fluid to the waste fluid container through the fluid supply tube, the connection tube and the connecting tube.

According to this method, since discharge of the waste fluid from the storage bag and supply of the additive fluid to the storage bag can be performed only by one connecting operation between the connecting tube and the connection tube, it is possible to reduce the necessary times of the tube connecting operations, which results in further improvement in operation.

Preferably, in these methods, a midsection of the connected tubes is sealed by a tube connecting apparatus and the section is then cut to form separate sealed end portions. By doing so, the storage bag can be stored separately from other bags or containers. Therefore, handling of the storage bag becomes easy and large space is not needed for storing the storage bag.

Preferably, the step of transferring preserving fluid from the reservoir fluid container can be carried out for several times with different fluid compositions and/or different volumes of fluid. By doing so, fluid replacements can be carried out under the condition suitable for storing the cells for instance, thus providing further improved preservation for the cells.

Other objects, functions and advantages of the present invention will be more fully understood from the following detailed descriptions of the preferred embodiments, taken in conjunction with the accompanying drawings.

DETAILED DESCRIPTION OF THE PREFERRED EMBODIMENTS

Figure 1:
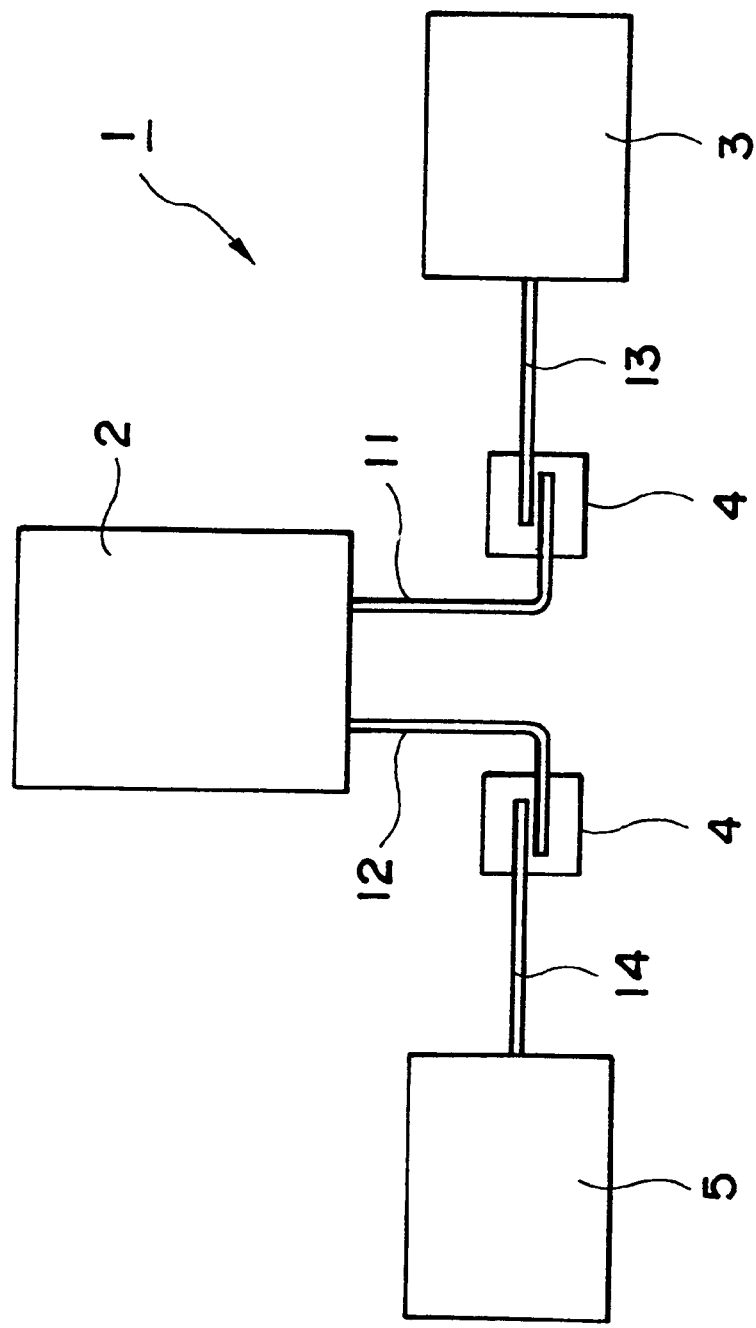
FIG. 1 is a schematic diagram illustrating an embodiment of a cell storage system according to the present invention.

Hereinafter, detailed descriptions of the preferred embodiments will be made with reference to the accompanying drawings. FIG. 1 is a schematic diagram showing an embodiment of a cell storage system 1 according to the present invention.

First, the present invention will be described for the case where this invention is applied to a blood storage system. Namely, the cell storage bag system 1 of the present invention comprises a storage bag 2, a fluid supply bag 3 which acts as a reservoir for containing a blood preserving fluid as an additive fluid, a waste fluid bag 5 for containing a supernatant discharged from the storage bag 2, and tubes connected to each bag, wherein predetermined tubes are connected to each other under sterile conditions by means of a tube connecting apparatuses 4.

Figure 2:
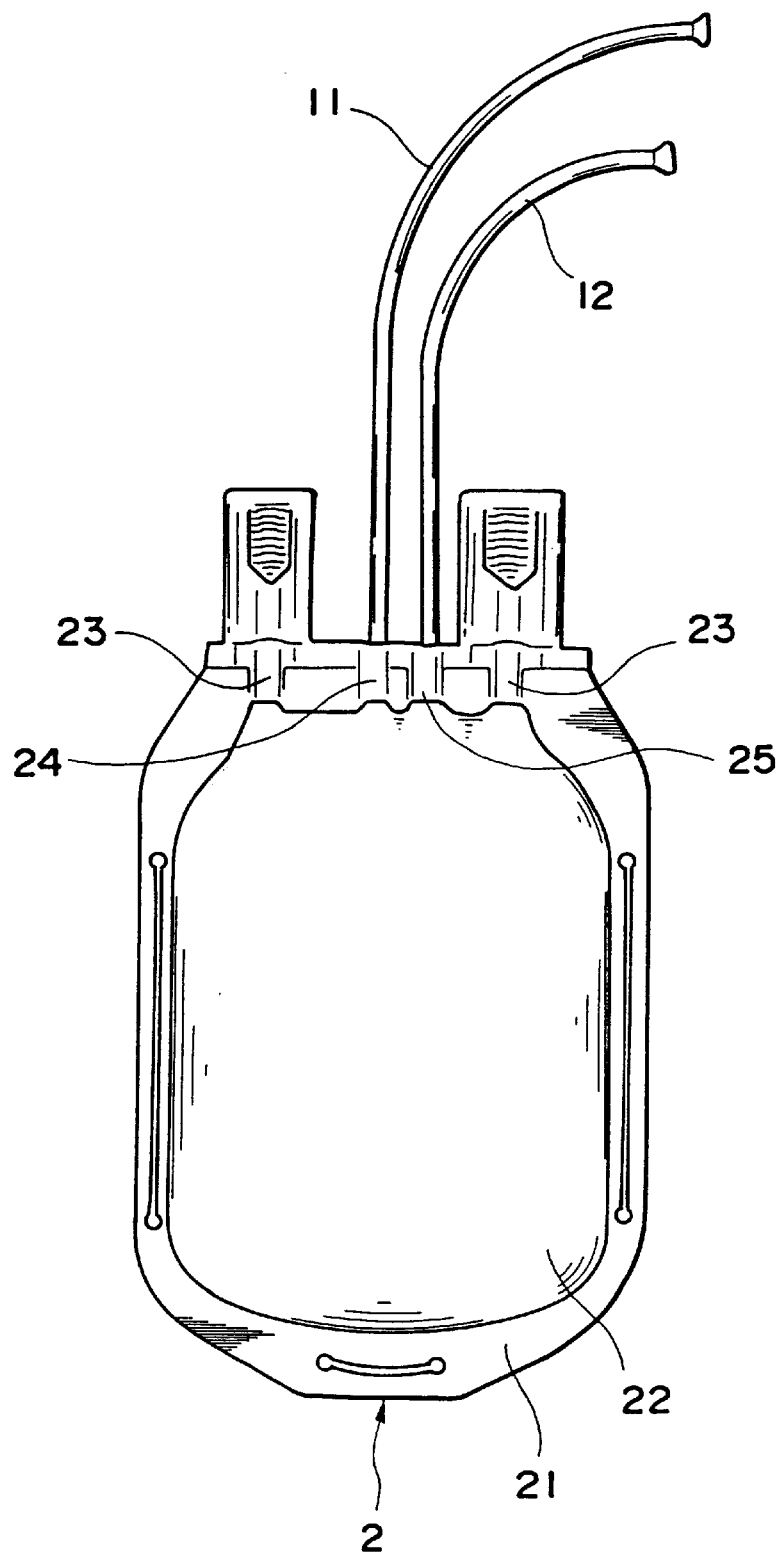
FIG. 2 is an entire front view illustrating a storage bag according to the present invention.

As shown in FIG. 2, the storage bag 2 is formed into a bag-shaped container by stacking two sheets made from a flexible resin and then forming a circumferential seal portion 21 by fusion (heat fusion, high frequency fusion and the like) or bonding. The space inside the storage bag 2 that is surrounded by the seal portion 21 forms a storage portion 22 that is used to store blood that has been extracted or blood components such as concentrated red blood cells that have been obtained by centrifuging such extracted blood.

As for a material used to construct the sheets, it is preferable for the material to have a moderate degree of air permeability, and to be suited for storing cells such as red blood cells, blood platelets and the like. Further, the material should have excellent heat resistance at the time when the storage bag 2 is undergoing high pressure steam sterilization. Moreover, it is preferred that the material have a sufficiently high elasticity so that the bag can withstand centrifuging operation and shaking preservation.

In this regard, suitable construction materials for such sheets include soft poly vinyl chloride or polyolefines such as polyethylene, polypropylene, ethylene-vinyl acetate copolymers and the like. In particular, soft poly vinyl chloride is preferred because it has sufficient heat resistance to withstand heat sterilization and can obtain a proper degree of elasticity to withstand centrifuging operation and shaking preservation. Furthermore, soft poly vinyl chloride is a low cost material and is an easy material to work with when manufacturing the bags.

Formed in an upper portion of the storage bag 2, as shown in FIG. 2, are two discharge ports 23, 23 equipped with peel tabs, and provided between the discharge ports 23, 23 are a guide port 24 and a waste liquid port 25. The guide port 24 is connected to one end of a first connecting tube 11, and the waste liquid port 25 is connected to one end of a second connecting tube 12, with the other ends of each tube 11, 12 being sealed, for example, by being fused.

Stored inside the storage portion 22 of the storage bag 2 are condensed red blood cells and the like that have been separated by means such as centrifuging and the like.

Figure 3:
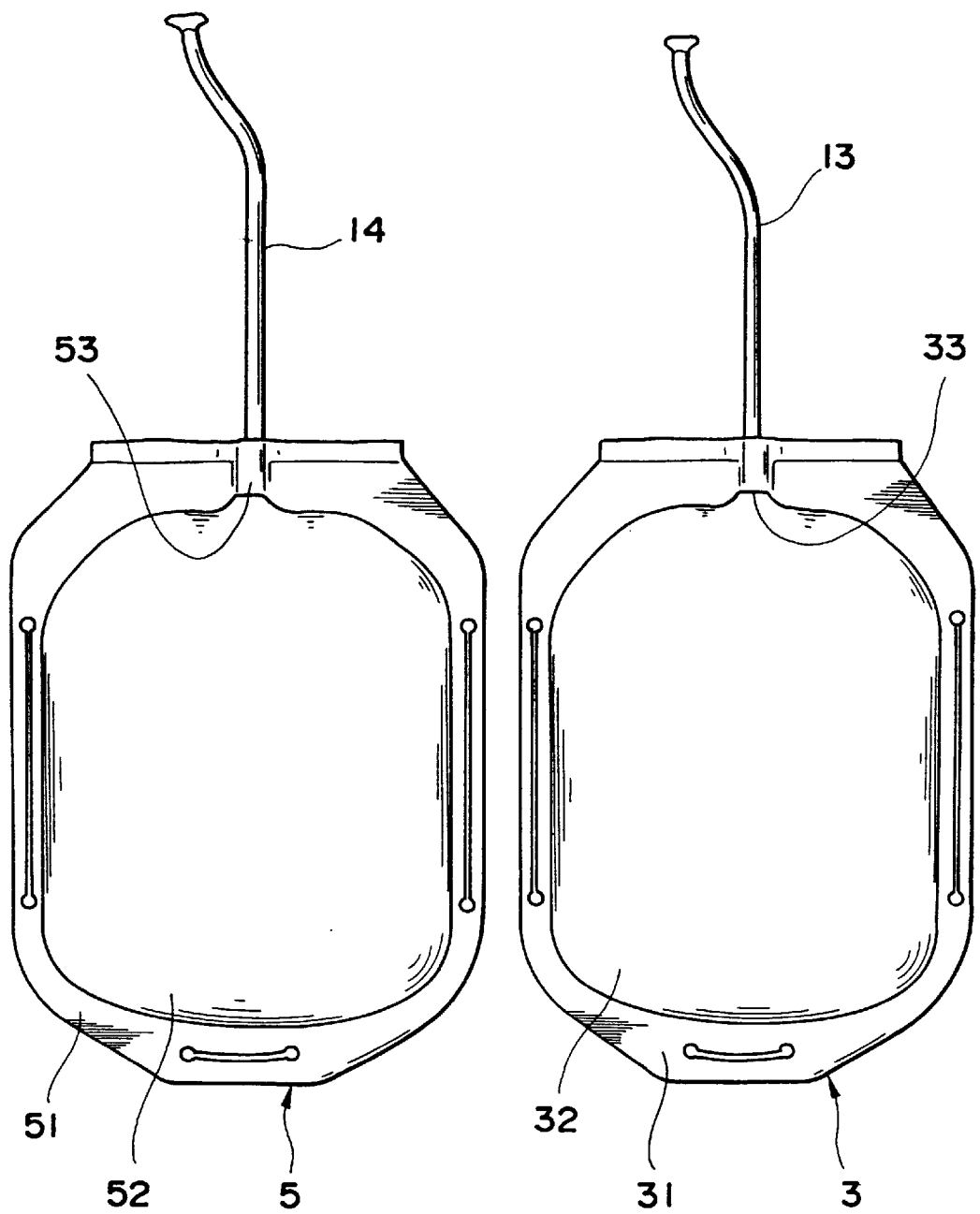
FIG. 3 is an entire front view illustrating a supply fluid bag and a waste fluid bag according to the present invention.

Now, as shown in the right side of FIG. 3, a fluid supply bag 3 is also formed into a bag-shaped container by stacking two sheets made from a soft poly vinyl chloride or the like and then forming a circumferential seal portion 31 by fusion (for example, heat fusion, ultrasonic frequency fusion or the like) or bonding. The space inside the fluid supply bag 3 that is surrounded by the seal portion 31 forms a storage portion 32 that is used to store a preserving fluid for preserving the concentrated red blood cells or the like, with the preserving fluid serving as an additive fluid that is added to the storage bag 2. Formed at an upper portion of the fluid supply bag 3 is a discharge port 33 to which is connected one end of a fluid supply tube 13, with the other end of the fluid supply tube 13 being sealed shut, for example, by being fused.

Next, as shown in the left side of FIG. 3, a waste fluid bag 5 is formed into a bag—shaped container by stacking two sheets made from a soft poly vinyl chloride or the like and then forming a circumferential seal portion 51 by fusion (for example, heat fusion, ultrasonic frequency fusion and the like) or bonding.

The space inside the waste fluid bag 5 that is surrounded by the seal portion 31 forms a storage portion 32 that is used to store waste fluid received from the storage bag 2. Formed at an upper portion of the fluid waste bag 3 is a guide port 53 to which is connected one end of a waste fluid tube 14, with the other end of the waste fluid tube 14 being sealed shut, for example, by being fused.

As for the tubes 11, 12, 13, 14, and tubes 11', 15, 16, 18 to be described below, they are all formed of materials which are capable of being cut, connected, and sealed by either softening or melting with applied heat. Specifically, these tubes are preferably formed of thermoplastic resins such as poly vinyl chloride, polyethylene, polypropylene, ethylene-vinyl acetate copolymers and the like, or materials whose main component is one of these materials. Among these materials, poly vinyl chloride is particularly preferred. Furthermore, in order to carry out easy and secure connections with the tube connecting apparatus 4, it is preferred that each tube be formed of the same or similar type of thermoplastic resin. In this regard, when using similar types of thermoplastic resins, it is preferred that their main components are in common or that such resinous materials have a high degree of compatibility at the time of undergoing heat fusion.

In addition to such properties, it is further preferred that the tubes to be connected have roughly the same outer and inner diameters.

In the construction described above, the fluid communication between the storage bag 2 and the fluid supply bag 3 and the fluid communication between the storage bag 2 and the waste fluid bag 5 are effected by connecting the first connecting tube 11 with the fluid supply tube 13 or the second connecting tube 12 with the waste fluid tube 14, respectively, by employing the tube connecting apparatuses 4.

Figure 4:
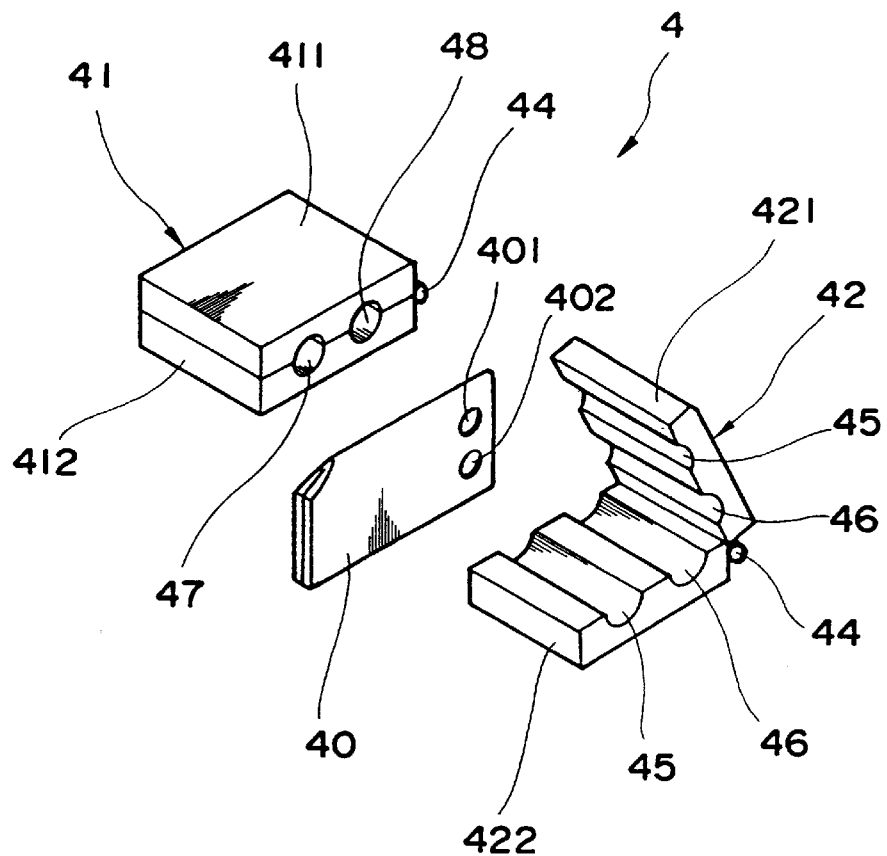
FIG. 4 is a perspective view illustrating one example of a construction of a tube connecting apparatus according to the present invention.
Figure 5:
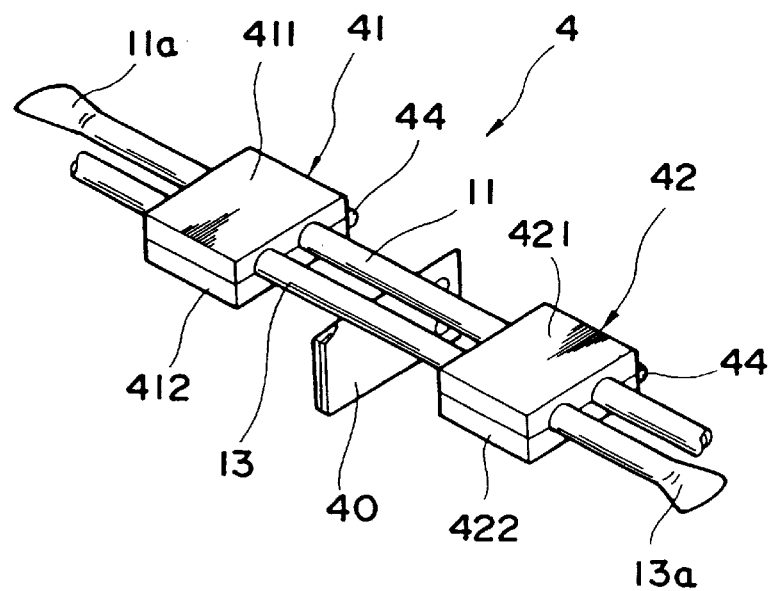
FIG. 5 is a perspective view illustrating one step in the process of connecting tubes by using the tube connecting apparatus shown in FIG. 4, according to the present invention.
Figure 6:
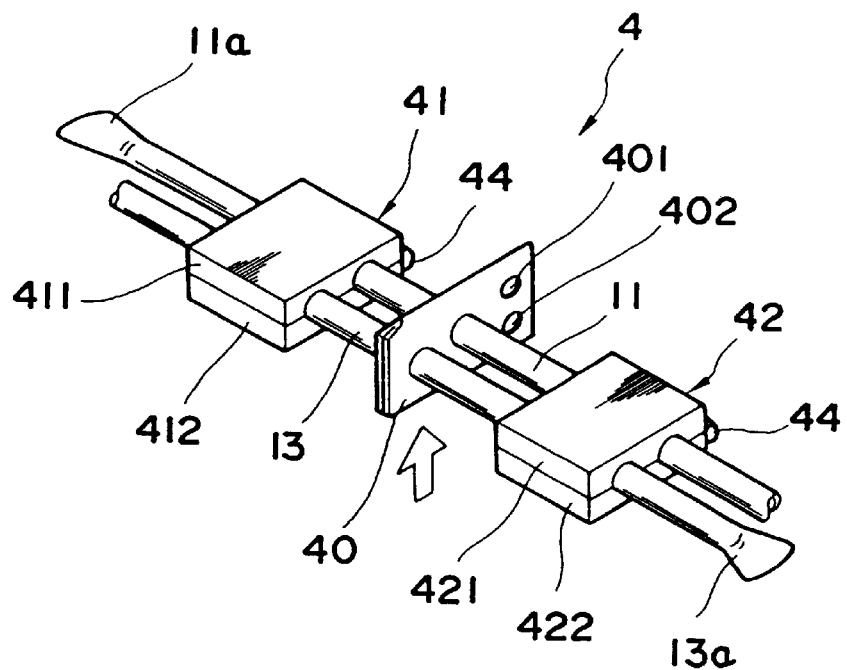
FIG. 6 is a perspective view illustrating another step in the process of connecting tubes by using the tube connecting apparatus shown in FIG. 4, according to the present invention.
Figure 7:
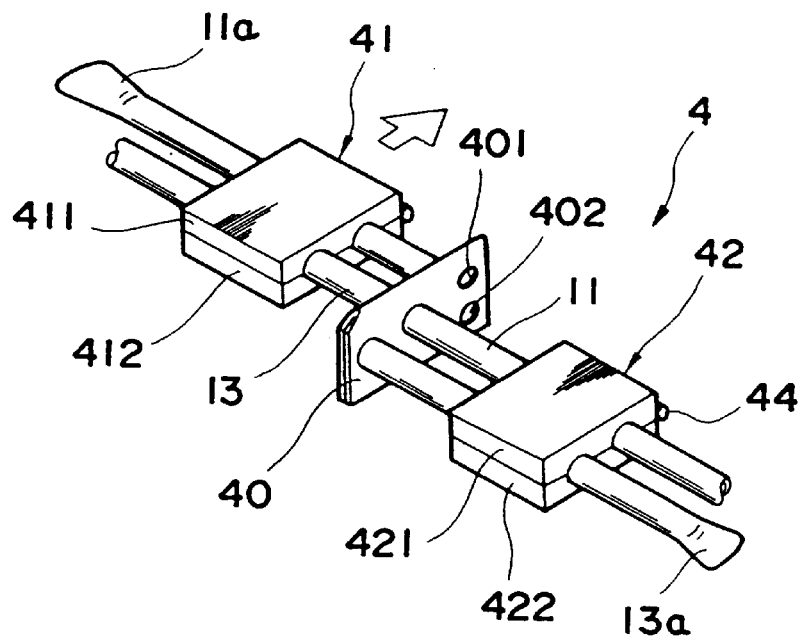
FIG. 7 is a perspective view illustrating another step in the process of connecting tubes by using the tube connecting apparatus shown in FIG. 4, according to the present invention.

Hereinafter, an explanation will be given for an example construction of the tube connecting apparatus 4. Namely, FIG. 4 shows a perspective view of an example construction of a tube connecting apparatus 4, and FIGS. 5–7 show perspective views of the connecting process for connecting the first connecting tube 11 and the fluid supply tube 13 by using the connecting apparatus 4. As shown in these drawings, the tube connecting apparatus comprises a pair of holders 41, 42 that act as movable connecting means for moving the tubes and connecting them together, and a wafer 40 served as heated cutting means that is insertable into and retractable out of a space between the holders 41, 42 for melting and cutting tubes that are held by the holders 41, 42. The wafer 40 is replaceable with a new one. The operation of these elements are understand with reference to FIGS. 5–7, which show the two tubes 11, 13, formed for example of poly vinyl chloride, being held by the holders 41, 42 so as to be roughly parallel to each other. Then as the heated cutting means 40 is inserted into the space between the holders 41, 42, the tubes 11, 13 are melted and cut, after which the holder 41 is moved to align the cut openings of the tubes 11, 13. Finally, the heated cutting means 40 is retracted or removed to bring the cut openings of the tubes 11, 13 together to form a fused joint between the two tubes 11, 13.

Now, as shown in FIG. 4, each of the holders 41, 42 are comprised of top and bottom holding plates 411, 412 and 421, 422, respectively, which are rotatable relative to each other by means of supporting axis 44. Formed in the opposing face (i.e., the inside surface) of each of the holding plates 411, 412 and 421, 422 are two grooves 45, 46 that run substantially parallel to each other and have half-circular shaped cross sections. Therefore, when the holding plates 411, 412 and 421, 422 are rotated to bring their opposing faces into contact with each other, the grooves 45, 46 of the top and bottom faces align with each other to define, respectively, tube supporting portions 47, 48 having circular shaped cross sections.

In this regard, it should be noted here that, even though not shown in the drawings, it is possible to provide a tube pinching means at the end portions of the holders 41 and 42 on the sides that face the heat cutting means 40 in order to flatten the tubes 11 and 13 to close off the inner passages thereof.

As for the wafer (cutting means) 40 of the present embodiment, it is a self-heating type heated plate made by folding a metal plate, such as a copper plate, and providing an insulation layer between the inside surface of such folded metal plate in order to form a resistor capable of generating heat in a desired pattern. As shown in the drawings, terminals 401, 402, which are located at both ends of the resistor, are exposed respectively from openings which formed at one end portion of each metal plate.

Next, a method of using the tube connecting apparatus will be described below.

First, as shown in FIG. 5, a fixed length of the tubes 11 and 13 are placed into the grooves 45, 46 of the holders 41, 42 so that the tubes 11, 13 are substantially parallel to each other with their closed ends 11a and 13a position on opposite sides of the holders 41, 42 to point in opposite directions relative to each other. Then, the holding plates 411, 412 and 421, 422 are closed to fixedly hold the tubes 11 and 13 within the holding portions 47 and 48, respectively.

Next, an electric current flowing means (not shown in the drawings) is used to flow an electric current having, for example, a 15–24 V potential between the terminals 401 and 402 so as to flow an electric current through the resistor of the heated cutting means 40. This causes the resistor to generate heat so as to heat the heated cutting means 40 to a temperature above the melting point of the tubes 11 and 13 (for example, 260–320 degrees).

While being maintained in this state, the heated cutting means 40 is moved in the upward direction, as shown in FIG. 6, to come into contact with the tubes 11 and 13, whereupon the heat from the heated cutting means causes the portion of the tubes 11 and 13 that are in contact with the heated cutting means to melt, and this allows the heated cutting means to cut through the tubes 11 and 13. At this time, because the cut end portions of the tubes 11 and 13 are in a fused or softened state due to the high temperature in the vicinity thereof, and because there is also no contact with outer portions, it is possible to maintain sterile conditions.

Figure 8:
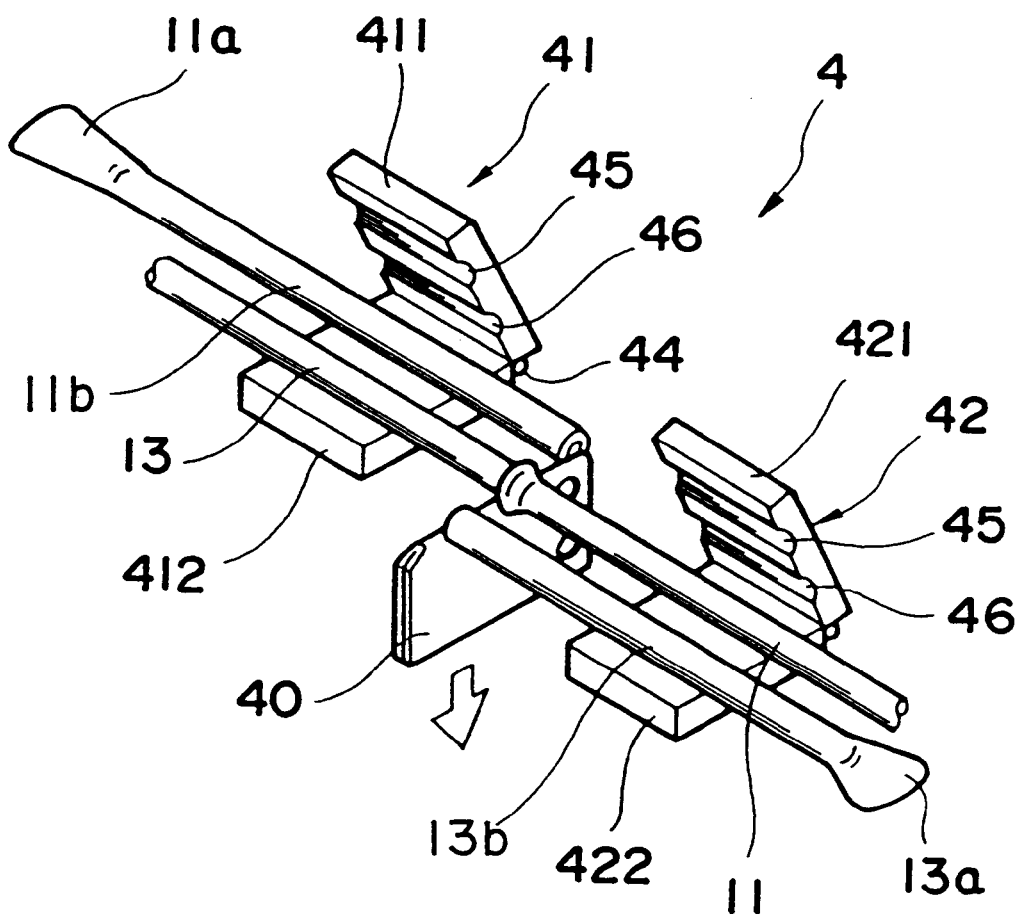
FIG. 8 is a perspective view illustrating another step in the process of connecting tubes by using the tube connecting apparatus shown in FIG. 4, according to the present invention.

Next, as shown in FIG. 7, with the cut end portions of the tubes 11 and 13 being maintained in a fused state, one of the holders, in this case holder 41, is moved so as to align the cut openings of the cut tubes 11 and 13 with each other, whereupon the holder 41 is fixed against further movement. Then, as shown in FIG. 8, the heated cutting means 40 is retracted in the downwards direction, and at roughly the same time the holder 42 and the holder 41 are moved for a tiny amount toward each other. This then causes the cut open ends of the tubes 11 and 13 to be pushed together to form a fused connecting portion 19 therebetween, and upon cooling the connecting portion 19 formed between the tubes 11 and 13 is completed.

Now, when the heated cutting means 40 is being retracted, portions of the inside surface of the tubes at and in the vicinity of the tube connecting portion 19 may become connected to each other, thereby blocking of part of the inner passage of the connected tubes. However, such blockage can be easily removed simply by pinching and rolling the tube connecting portion 19 between, for example, the thumb and a finger of one hand, to establish the connections between the portions of the inside surface of the tubes.

Here it is to be noted that by using the type of heated cutting means 40 described above throughout all the series of steps from cutting to connecting the tubes 11 and 13, the cut ends of the tubes and the portions in the vicinity thereof are either in a fused or softened state at a high temperature. Moreover, until such cut ends are brought into contact with each other to be fused together to form the tube connecting portion 19, they are in constant contact with the heated cutting means 40, and throughout the entire process there is no other outside contact. Therefore, it is possible to maintain virtually complete sterile conditions throughout the entire process.

After tubes 11 and 13 have been connected to each other, the left over tube segments 11b and 13b, having the closed off ends 11a and 13a, are discarded.

Then, before the tube connecting apparatus is to be used again for connecting another pair of tubes, the used heated cutting means 40 is replaced by a new heated cutting means 40, and the used heated cutting means 40 is discarded. Namely, it is preferred that the heated cutting means 40 be a single use element that is used only once in the tube connecting apparatus 4 and then discarded.

Also, it is preferred that the heated cutting means 40 be of a type which allows a determination to be easily made as to whether the heated cutting means 40 has already been used or is a new unused element.

As for connecting the second connection tube 12 and the waste fluid tube 14, a tube connecting apparatus 4 is used to carry out such connection in the same manner as described above.

In carrying out tube connections with the tube connecting apparatus 4, it is preferred that the tubes have an outer diameter in the range of 4.0–5.0 mm and an inner diameter in the range of 2.5–3.5 mm.

Hereinafter, an example of a cell storage method using the cell storage bag system of the present will be described in a step-wise manner below for the specific case of storing concentrated red blood cells.

1-1: A blood bag containing extracted blood is centrifuged to separate the blood into three components: including blood plasma, baffy coat and red blood cells.

1-2: The upper layer containing the blood plasma and the middle layer containing the baffy coat are transferred to a separate blood component preserving bag (not shown in the drawings), leaving the bottom layer of concentrated red blood cells in the blood bag. At this time, the blood introducing tube of the blood bag and the other tube connected at one end thereof to the separate blood component preserving bag are sealed at a midsection thereof using a heat fusing means, and then these sealed portions are cut and separated to form sealed end portions. In this state, the blood bag forms a storage bag 2, with the tubes having the cut and sealed end portions forming the first and second connecting tubes 11 and 12, respectively.

1-3: The connecting tube 11 and the fluid supply tube 13 of the fluid supply bag 3 are connected using the tube connecting apparatus 4 in the manner described above, and then an appropriate amount of preserving fluid is transferred from the fluid supply bag 3 to the storage bag 2 via the connected tubes 11 and 13. Examples of the ways to carry out the transfer of storage fluid from the fluid supply bag 3 to the storage bag 2 include applying pressure to the fluid supply bag 3, placing the fluid supply bag 3 at a position higher than the storage bag 2 to allow the storage fluid to drain down, or utilizing a roller pump to pump the storage fluid to the storage bag 2.

Then, after the transfer of the storage fluid to the storage bag 2 has been completed, a seal is formed at a section along either the connecting tube 11 or the fluid supply tube 13 using a heat fusing means, and then this sealed section is cut and separated to form a sealed end tube. By carrying out these steps, the tube is sealed off by forming the sealed portion which is then cut to form a sealed end portion. As a result, no outside air can enter into the system, and this makes it possible to ensure that a sterile environment is maintained within the tube.

1-4: After a prescribed storage period has passed, the preserving fluid is replaced, and at such time a blood extraction tube having a sealed end is used as the second connecting tube 12. Here, the first step involves centrifuging the storage bag 2 to form a large upper layer comprising the storage fluid and a lower layer comprising concentrated red blood cells.

1-5: The second connecting tube 12 and a waste fluid tube 14 of an empty waste fluid bag 5 are connected by using the tube connecting apparatus 4 in the same manner described above. Then by either applying pressure to the storage bag 2 or by arranging a roller pump at a position along the connected tubes 12 and 14, the separated upper layer of fluid in the storage bag 2 is transferred to the waste fluid bag 5 via the connected tubes 12 and 14. After completing this step of discharging from the storage bag 2 the upper layer of fluid containing the old storage fluid, a seal is formed at a portion along either the second connecting tube 12 or the waste fluid tube 14 by using the heat fusing means, and then this sealed portion is cut and separated to form a sealed end tube.

1-6: Next, the connecting tube 11 and the fluid supply tube 13 of the fluid supply bag 3 are connected by using the tube connecting apparatus 4 in the same manner as was described above, and then, in the same manner as was described in steps 1–3, an appropriate amount of storage fluid is transferred from the fluid supply bag 3 to the storage bag 2. Then, after the transfer of the storage fluid to the storage bag 2 has been completed, a seal is formed at a portion along either the connecting tube 11 or the fluid supply tube 13 by using the heat fusing means, and then this sealed portion is cut and separated to form a sealed end tube.

By repeating the steps 1-3 through 1-6 above, it is possible to replace the storage fluid any number of times. Moreover, the above system construction is advantageous in that it makes it possible to achieve a more efficient replacement of fluids without the risk of contamination. This is accomplished by the use of different paths to transfer the storage fluid and the waste fluid, which thus prevents any mixing of the waste fluid and the newly added storage fluid.

With regards to an additive fluid to be added to the concentrated red blood cells contained in the storage bag 2, the examples include a blood preserving fluid, a blood rejuvenating fluid, a physiological saline solution used for cleaning the blood, and the like.

In this connection, a list of the types of storage solutions and their corresponding compositions are given in Table 1. Furthermore, Table 2 lists the type and composition of preserving fluids (having anti-coagulating agents) that are initially put inside the blood extraction bag. And Table 3 lists the type and composition of rejuvenating fluids.

TABLE 1

| | Composition of the additive fluid (preserving fluid) ( ) means absolute anhydrous | | | | | | | | | |
|---|---|---|---|---|---|---|---|---|---|---|
| name of the additive fluid | S.A.G.M. | ADSOL (AS-1) | Nutricel (AS-2) | Nutricel (AS-3) | PAGG-S | SAGP-maltose | Circle Pack | (AS-4) | OPTISOL (AS-5) | MAP (AS-5) |
| composition of the additive fluid (mg) | | | | | | | | | | |
| sodium chloride (S) | 877 | 900 | 718 | 410 | 420 | 327 | 718 | 638 | 877 | 497 |
| adenine (A) | 17 | 27 | 17 | 30 | 24.6 | 19 | 18.4 | 17 | 30 | 14 |
| dextrose(monohydrate) (G) | 900 | 2200 | 396 | 1100 | 940 | 554 | (721) | | 900 | (721) |
| mannitol (M) | 525 | 750 | | | | | | | 525 | 1457 |

TABLE 1-continued

Composition of the additive fluid (preserving fluid)
( ) means absolute anhydrous

| name of the additive fluid | S.A.G.M. | ADSOL (AS-1) | Nutricel (AS-2) | Nutricel (AS-3) | PAGG-S | SAGP-maltose | Circle Pack | (AS-4) | OPTISOL (AS-5) | MAP (AS-5) |
|---|---|---|---|---|---|---|---|---|---|---|
| citric acid | | | | 42 | | | 42 | | | 20 |
| sodium citrate | | | 588 | 588 | | | | 588 | | 150 |
| sodium dihydrogen phosphate | | | | 276 | 288 | | | | | 94 |
| disodium hydrogen phosphate | | | 285 | | 110 | 199 | 312 | 86 | | |
| guanosine | | | | | 40.8 | | | | | |
| sorbitol | | | | | 100 | | | | | |
| maltose | | | | | | 1436 | | | | |
| ascorbate-2-phosphate | | | | | | | | 298 | | |
| standard volume of blood extraction (ml) | 450 | 450 | 450 | 450 | 450 | 450 | 450 | 450 | 450 | 400 |
| volume of the additive fluid (mg)* | 100 | 100 | 100 | 100 | 100 | 70 | 100 | 75 | 100 | 90 |

*: added volume to concentrated red blood cells obtained from the standard volume of blood extraction

TABLE 2

Types of the preserving fluids contained in blood extraction bag and composition thereof
( ) means absolute anhydrous

| composition (per 100 ml) | ACD-A | CPD | CPDA-1 | CPDA-2 | CPD-Adenine | CP2D |
|---|---|---|---|---|---|---|
| sodium citrate | 2.20 g | 2.63 g | 2.63 g | 2.63 g | 2.63 g | 2.63 g |
| citric acid | 0.80 g | 0.327 g | 0.327 g | 0.327 g | 0.327 g | 0.327 g |
| glucose | (2.20 g) | (2.32 g) | (2.90 g) | (4.06 g) | (2.32 g) | (4.64 g) |
| sodium dihydrogen phosphate | | 251 mg | 251 mg | 251 mg | 251 mg | 251 mg |
| adenine | | | 27.5 mg | 55 mg | 27.58 mg | |

TABLE 3

Composition of rejuvenating fluids (mM) (per 50 ml)

| Composition/types | MAIP | PMAIP | PMAIP$_2$ | CMAIP$_2$ | PIGPA | PIP |
|---|---|---|---|---|---|---|
| mannitol | 180 | 180 | 180 | 180 | | |
| adenine | 5 | 5 | 5 | 5 | 5 | 5 |
| inosine | 40 | 40 | 40 | 40 | 50 | 100 |
| sodium dihydrogen phosphate | 8 | 4 | 8 | 8 | | 25.6 |
| disodium hydrogen phosphate | 16 | 8 | 16 | 16 | 50 | 70.4 |
| sodium chloride | 50 | 20 | 20 | 20 | 154 | |
| dextrose | | | | | 100 | |
| sodium citrate | | | | 8 | | |
| pyruvic acid | | | | | 50 | |
| sodium pyruvate | | 50 | 50 | 50 | | 99 |
| pH | 6.8–7.2 | 6.8–7.2 | 6.8–7.2 | 6.8–7.2 | 7.2 | 6.7–7.4 |

As for the fluid supply bag 3 and the waste fluid bag 5, they need not be limited to bags having a capacity to hold only enough fluid for one fluid replacement of the additive fluid. It is possible to design these bags so as to have large enough capacities which allow a single fluid supply bag 3 to contain a volume of the additive fluid for several replacements, and which allow a single waste fluid bag 5 to receive a volume of the waste fluid for several times of collections of the waste fluid. By doing so, it becomes possible to supply the additive fluid from the same container and to collect the waste fluid by the same container in each replacement of the additive fluid. Further, the fluid supply bag 3 may be formed to have the same characteristic and shape as those of the storage bag so that it is also possible to transfer the cells from the storage bag 2 to the fluid supply bag 3 after the waste fluid waste has been discharged from the storage bag 2.

Figure 9:
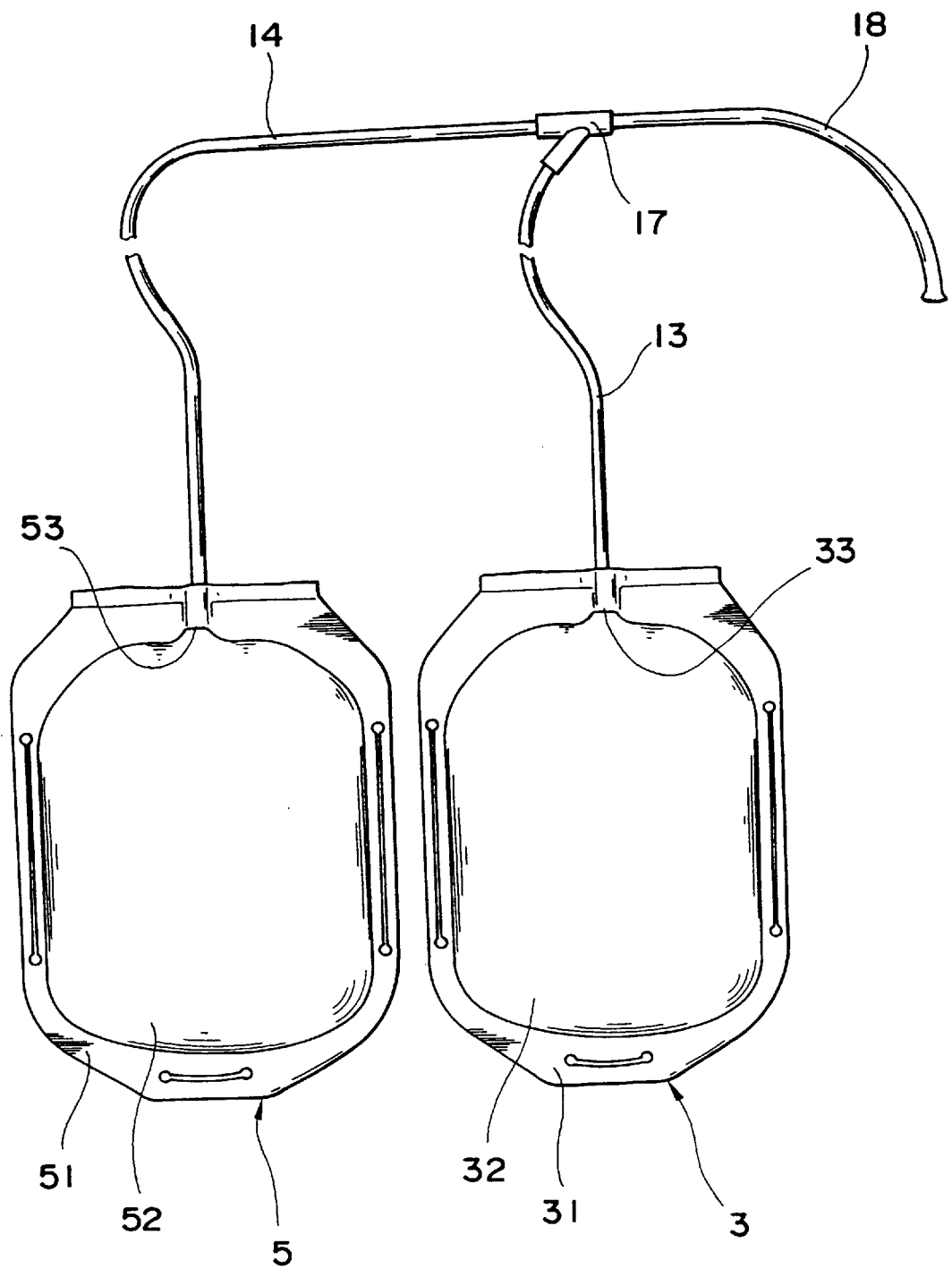
FIG. 9 is an entire front view of an example of a bag arrangement comprised of a supply fluid bag and a waste fluid bag, according to the present invention.
Figure 10:
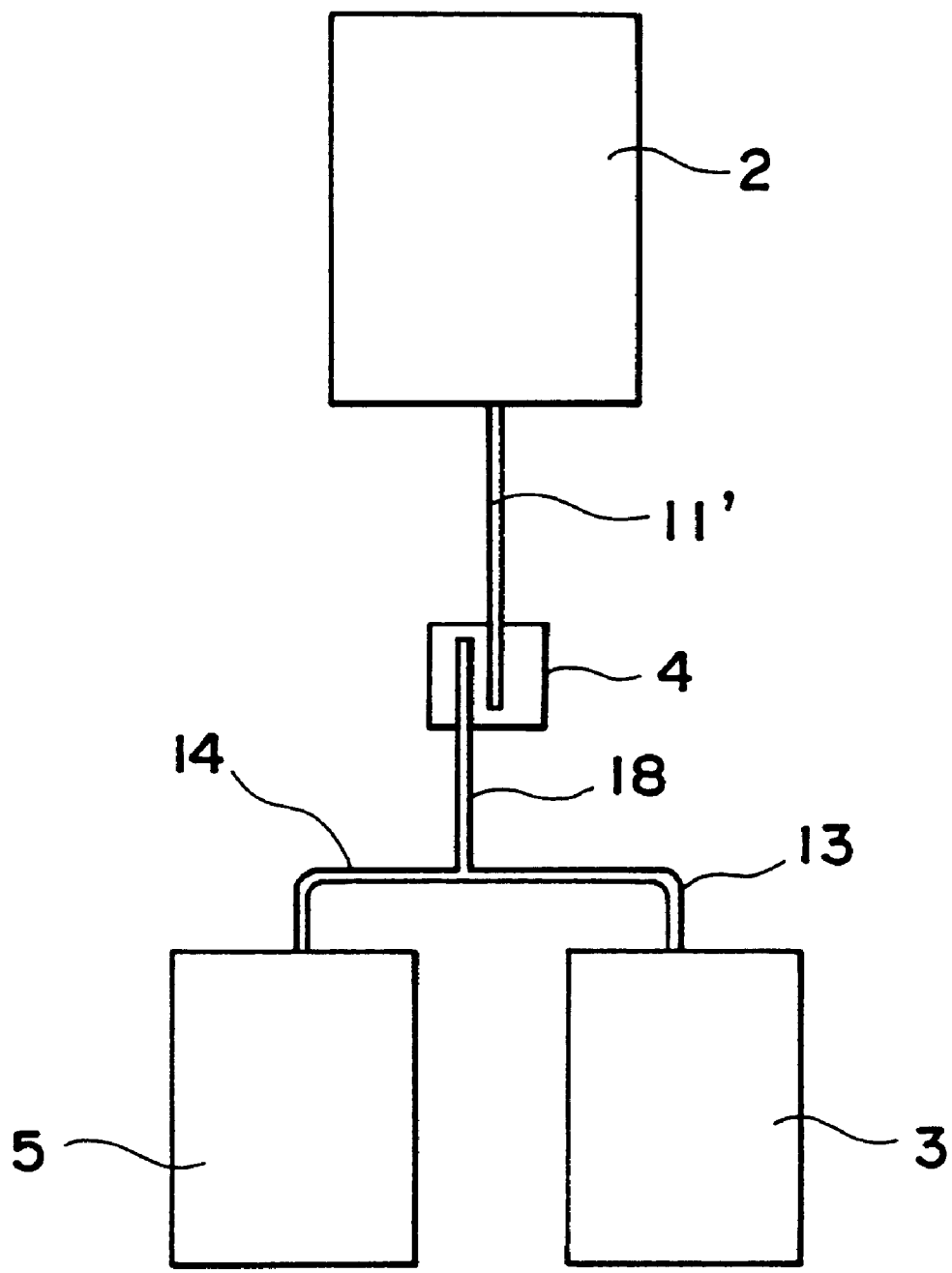
FIG. 10 is a schematic diagram illustrating another embodiment of a cell storage bag system that incorporates a two bags arrangement.

FIGS. 9 and 10 show a cell storage bag system according to another embodiment of the present invention. As shown in these drawings, the fluid supply tube 13 of the fluid supply bag 3 communicates with the waste fluid tube 14 of the waste fluid bag 5 by means of a branch connector 17 which is connected to a single communicating tube 18 that is adapted to be connected to a connecting tube of the storage bag 2. In this case, only one connecting tube 11' is needed as the tube to be connected to the storage bag 2, and therefore only one tube connecting operation is required. As a result, this arrangement makes it possible to obtain an improved work efficiency.

Moreover, the use of the cell storage bag system according to the present invention is no limited to the case where the storage bag 2 is to be stored in itself. It is also possible to apply this invention to the case where a fluid supply bag or a waste fluid bag is connected to a plurality of blood bags which are communicated with each other by means of tubes or a mulitiple bag in which a blood bag is connected to other bags such as bags for containing blood plasma and the like, via tubes.

Figure 11:
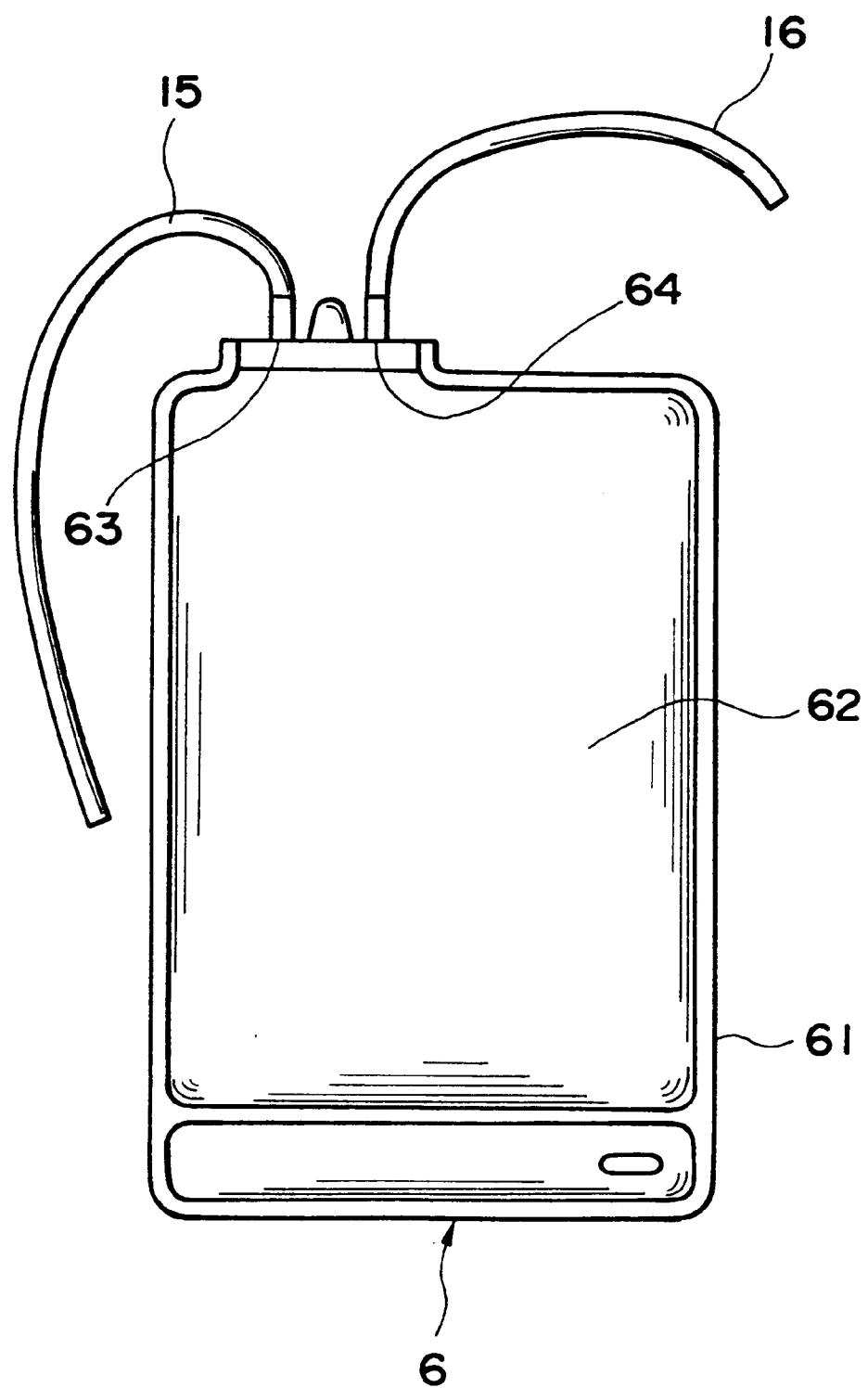
FIG. 11 is an entire front view of an example of the construction of a preserving bag used in cell cultivation, according to the present invention.

Hereinafter, the description will be made with reference to the case which this invention is applied to a cell cultivating system. As shown in FIG. 11, a cell cultivating system comprises a storage bag 6 which acts as a cell cultivating bag. The storage bag 6 is formed into a bag-shaped container by stacking two sheets made from a flexible resin material and then forming a circumferential seal portion 61 by fusion (for example, heat fusion, high frequency fusion or the like) or bonding. The space defined inside the storage bag 6 that is surrounded by the seal portion 61 forms a storage portion 62 that is used to store a liquid medium.

In this connection, there are no particular limitations to the types of cells that may be cultivated by using the cell cultivation system according to the present invention, and examples include various viruses and bacterium, yeasts, plant cells and the like, which can all be cultivated to spread throughout the liquid medium contained within the storage bag 6. For the purpose of cultivating cells, the material used for making the sheets that form the storage bag 6 should have excellent air permeability. In this regard, polyolifine is the material that is most preferred.

As is shown in FIG. 11, an inlet port 63 and a waste fluid port 64 are formed in an upper portion of the storage bag 6, and connected to the inlet port 63 and the waste fluid port 64 are, respectively, a first connecting tube 15 and a second connecting tube 16.

In this embodiment, a fluid supply bag 3 and a waste fluid bag 5 are the same as those that described previously above. In this case, the fluid supply bag 3 contains a liquid medium for cell cultivation and the waste fluid bag 5 is an empty bag.

Now, in the same manner as was described for the case of the storage of blood, the tube connecting apparatus 4 is used to connect the second connecting tube 16 with the waste fluid tube 14 and the first connecting tube 15 with the fluid supply tube 13.

As for separating the liquid medium from the cells that are being cultivated in the storage bag 6, many methods may be utilized, in which examples include centrifuging or filtering the contents of the storage bag 6.

Next, a description given below is the steps of a cell cultivating method utilizing the cell cultivating system of the present invention.

2-1: When it is time to replace the liquid medium, the storage bag 6 is removed from a carbon dioxide incubator, and then the second connecting tube 16 and the waste fluid tube 14 are connected by using the tube connecting apparatus 4 in the same way as was described previously above.

2-2: Next, the old liquid medium is transferred from the storage bag 6 to be collected in the waste fluid bag 14. Examples of methods to carry out such transfer include applying pressure to the storage bag 6 by lightly pressing the storage bag 6 or squeezing the storage bag 6 from the bottom, placing the storage bag 6 at a position higher than the waste fluid bag 5 to allow the waste fluid to drain down, or utilizing a roller pump positioned along the tube to pump the waste fluid to the waste fluid bag 5.

To separate the cells from the liquid medium, the contents of the storage bag 6 may, for example, be centrifuged or filtered, and such separation may be carried out either before or after the tubes 14 and 16 are connected.

2-3: The connecting portion that connects the second connecting tube 16 and the waste fluid tube 14 is then sealed shut by using a heat fusing means, and then this sealed portion is cut and separated to form a sealed end. Next, the tube connecting apparatus 4 is used to connect the first connecting tube 15 and the fluid supply tube 13.

2-4: In the same manner as was described previously above, fresh liquid medium that acts as an additive fluid is supplied to the storage bag 6 from the fluid supply bag 3. Then, after an appropriate amount of liquid medium has been supplied to the storage bag 6, the connecting portion that connects the first connecting tube 15 and the fluid supply tube 13 is then sealed shut by using a heat fusing means, and then this sealed portion is cut and separated to form a sealed end.

2-5: Upon completion of the replacement of the liquid medium as carried out by the above steps, the storage bag 6 is returned to the carbon dioxide incubator.

The above steps 2-1 through 2-5 may be carried out in each time when it is necessary to replace the liquid medium. In this connection, as only the storage bag 6 is required to be placed inside the incubator, it is not necessary for the incubator to have a large holding capacity, and this makes it possible to more effectively use the space of the incubator. Furthermore, as only a single bag is placed in and removed from the incubator, such easy handling makes the work involved in using the storage bag to proceed at a faster pace.

Next, described below is a detailed description of a specific embodiment of a cell storage bag system used as a blood storage bag system according to the present invention.

<Construction of the Storage Bag System>

A cell storage bag system is provided with the construction shown in FIGS. 9 and 10. The particulars of each element are as follows.

I. Storage Bag

A storage bag to be used as a blood bag is made from sheets of soft polyvinyl chloride, the particulars of which are given below:

Sheet thickness: 0.36 mm

Bag capacity: 400 ml

II. Fluid Supply Bag & waste fluid Bag

The fluid supply bag and the waste fluid bag are made from sheets of soft polyvinyl chloride so as to have the same construction and the same holding capacity, namely, 300 ml.

III. Tubes

All of the tubes connected to the bags described above are made of soft polyvinyl chloride so as to have an outer diameter of 4.4 mm and an inner diameter of 3.0 mm. As for the type of the soft poly vinyl chloride used to construct these tubes, it is chosen so as to have a melting point of 170 degrees Celsius.

IV. Tube Connecting Apparatus

Using applied heat to cut and fuse the tubes, a heated cutting means (wafer) is formed by folding 2 copper plates with a resistor placed therebetween and two openings formed in the metal plates for exposing terminals to allow an electric current to be passed through the resistor so that the heated cutting means becomes a self-heating body capable of generating heat at a temperature of 260 degrees Celsius.

The holders shown in FIG. 4 are used for this apparatus, in which the diameter of each groove in the holders is set to 4 mm with a semi-circular shape, and the gap of the adjacent grooves is set to 2 mm.

In order to move the holder, use is made of a holder driving means (not shown in the drawings) equipped with a motor, a converter and a cam mechanism so as to move one holder in the direction along which the tubes are arranged, and to move the other holder in the direction parallel to the lengthwise direction of the tubes.

For the heated cutting means, use is made of a cutting means driving means (not shown in the drawings) equipped with a motor, a converter and a cam mechanism so as to move the cutting means upwardly to be inserted into the space between the holders and downwardly to retract the cutting means from the space between the holders.

In this regard, it should be noted that the particulars of the tube connecting apparatus are disclosed in Laid-open Utility Model Publication No. 6-26877 which was filed by the applicant.

<Method for Storing Red Blood Cells>

First, the extracted blood that is contained within the blood bag is centrifuged to separate the red blood cells from the blood plasma and baffy coat, and then the blood plasma and baffy coat are transferred to other bags, leaving the concentrated red blood cells remaining in the storage bag. Also existing in the bag is ACD-A fluid which was previously put into the storage bag to act as an anti-coagulating agent. Then the red blood cells are stored for four weeks, but after two weeks the storage fluid is replaced with MAP fluid using the method described below.

3-5: Lastly, the communicating tube 18 is sealed shut by using a heat fusing means, and then this sealed portion is cut and separated to form a sealed end.

The above steps 3-1 through 3-5 are carried out every two weeks.

<Results>

Shown in Tables 4 and 5 are measurements of the glucose and lactic acid levels taken every two weeks for red blood cells stored at 4 degrees Celsius and 0 degrees Celsius.

TABLE 4 glucose
(Measuring method: "Glucose B Test Wako" provided by Wako Junyaku, Inc.)
Unit: mg/dl   n = 6   average value ± SD

| weeks |  | 0 | 2 | 4 | 6 | 8 | 10 | 12 |
|---|---|---|---|---|---|---|---|---|
| 4° C. | Example | 580 ± 40 | 495 ± 55 | 400 ± 30 | 560 ± 50 | 470 ± 40 | 600 ± 60 | 500 ± 55 |
|  | Control | 620 ± 25 | 480 ± 45 | 405 ± 40 | 395 ± 40 | 330 ± 40 | 300 ± 50 | 290 ± 60 |
| 0° C. | Example | 590 ± 50 | 505 ± 45 | 430 ± 40 | 590 ± 50 | 500 ± 40 | 610 ± 60 | 520 ± 55 |
|  | Control | 600 ± 45 | 500 ± 50 | 425 ± 35 | 400 ± 35 | 375 ± 45 | 340 ± 55 | 325 ± 70 |

(Note)
Example: Preserving fluid was replaced after four weeks, and thereafter the fluid was not replaced for every two weeks.
Control: Preserving fluid was initially added, and thereafter the preserving fluid was not replaced.

TABLE 5 lactic acid
(Measuring method: "Lactate Test" provided by Boerhinger Mannheim-Yamanouchi, Inc.)
Unit: mg/dl   n = 6   average value ± SD

| weeks |  | 0 | 2 | 4 | 6 | 8 | 10 | 12 |
|---|---|---|---|---|---|---|---|---|
| 4° C. | Example | 25 ± 5 | 98 ± 10 | 170 ± 10 | 102 ± 12 | 182 ± 20 | 138 ± 28 | 140 ± 5 |
|  | Control | 24 ± 4 | 99 ± 8 | 165 ± 12 | 234 ± 16 | 245 ± 18 | 263 ± 16 | 270 ± 16 |
| 0° C. | Example | 26 ± 3 | 76 ± 8 | 156 ± 10 | 88 ± 14 | 128 ± 12 | 82 ± 28 | 80 ± 5 |
|  | Control | 24 ± 5 | 80 ± 6 | 155 ± 12 | 186 ± 12 | 205 ± 16 | 228 ± 10 | 252 ± 12 |

(Note)
Example: Preserving fluid was replaced after four weeks, and thereafter the fluid was not replaced for every two weeks.
Control: Preserving fluid was initially added, and thereafter the preserving fluid was not replaced.

3-1 The storage bag is placed in a centrifugal separator to separate the preserving fluid from the concentrated red blood cells. In this case, the centrifugal separator used is DPR6000 (Product Name) of IEC corporation, which was operated at 3300 rpm (3000 G) for 5–7 minutes.

3-2: Next, a closed end portion of the communicating tube 18, which communicates with the two bag arrangement comprised of the fluid supply bag 3 and the waste fluid bag 5, is connected to a closed end portion of the connecting tube 11' of the storage bag 2 by using the tube connecting apparatus 4.

3-3: Then the fluid supply tube 13 of the fluid supply bag 3 is closed off by using a clamp (hereinafter, referred to as "klemme" (Germany)) to block off the inside flow path of the fluid supply tube 13, after which the separated upper fluid layer (comprised of storage fluid) in the storage bag 2 is transferred and collected in the fluid waste bag 5 via tubes 11', 18 and 14.

3-4: Next, the waste fluid tube 14 of the waste fluid bag 5 is closed off by using a klemme to block off the inside flow path of the waste fluid tube 14, and then the inside fluid path of the fluid supply tube 13 is opened up by removing the klemme from the fluid supply tube. Then MAP fluid is transferred from the fluid supply bag 3 via tubes 13, 18 and 11' to the storage bag 2 where it is added to the concentrated red blood cells to form a mixture therewith.

As shown in Tables 4 and 5, it was confirmed that red blood cells stored at 4 degrees Celsius can have substantially the same metabolic state as red blood cells stored for two weeks under the same conditions. Further, it was also confirmed that red blood cells stored at 0 degrees Celsius can have substantially the same metabolic state as red blood cells stored for two weeks under the same conditions.

<Rejuvenating Fluid Treatment>

4-1: In the above method, when the storage fluid was replaced, it was carried out at 0 degrees Celsius. And then after 12 weeks, the storage bag was removed from a cold storage and allowed to warm up to room temperature. Upon reaching a temperature that is at or close to room temperature, the storage bag was centrifuged.

4-2: Next, the communicating tube 18, which communicates with a two bag arrangement comprised of the fluid supply bag 3 and the waste fluid bag 5, was connected to the connecting tube 11' of the storage bag 2 using the tube connecting apparatus 4, and then the fluid supply tube 13 of the fluid supply bag 3 is closed off by using a klemme to block off the inside flow path of the fluid supply tube 13, after which the separated upper fluid layer in the storage bag 2 is transferred and collected in the waste fluid bag 5 via tubes 11', 18 and 14.

4-3: Then, the waste fluid tube 14 of the waste fluid bag 5 was closed off by using a klemme to block off the inside flow path of the waste fluid tube 14, and then the inside fluid path of the fluid supply tube 13 was opened up by removing the klemme from the fluid supply tube 13. Then rejuvenating fluid was transferred from the fluid supply bag 3 via tubes 13, 18 and 11' to the storage bag 2 where it was added to the concentrated red blood cells to form a mixture therewith. As for the volume of added rejuvenating fluid, it was chosen to have roughly equivalent to the volume of concentrated red blood cells stored in the storage bag 2. Thereafter, the communicating tube 18 is sealed shut using a heat fusing means, and then this sealed portion is cut and separated to form a sealed end.

4-4: The storage bag 2 is then heated at a temperature of 37 degrees Celsius for 60 minutes.

4-5: Next, the storage bag 2 is centrifuged once more, and then a communicating tube 18, which communicates with a two bag arrangement comprised of a physiological saline solution (fluid supply) bag 3 and a waste fluid bag 5, is connected to the connecting tube 11' of the storage bag 2 again by using the tube connecting apparatus 4. As for the centrifuging step, it is carried out by using the centrifugal separator DPR6000 (Product Name) of IEC corporation, which was operated at 3300 rpm (3000 G) for 5–7 minutes.

4-6: Then the fluid supply tube 13 of the physiological saline solution bag 3 is closed off by using a klemme to block off the inside flow path of the fluid supply tube 13, after which the separated upper fluid layer in the storage bag 2 is transferred and collected in the waste fluid bag 5 via tubes 11', 18 and 14.

4-7: Next, the waste fluid tube 14 of the waste fluid bag 5 is closed off by using a klemme to block off the inside flow path of the waste fluid tube 14, and then the inside fluid path of the fluid supply tube 13 is opened up by removing the klemme from the fluid supply tube 13. Then saline solution is transferred from the physiological saline solution bag 3 via tubes 13, 18 and 11' to the storage bag 2 where it is added to the concentrated red blood cells to form a mixture therewith.

4-8: Then, the communicating tube 18 is sealed shut using a heat fusing means, and then this sealed portion is cut and separated to form a sealed end.

4-9: For washing the red blood cells stored in the storage bag 2, the steps 4-5 through 4-8 are repeated two or three times. In this case, washing is carried out by using 1000 ml of physiological saline solution. Lastly, the treatment of the red blood cells is completed by adding a volume of saline solution equivalent to the volume of red blood cells stored in the storage bag 2.

<Results>

After the rejuvenating treatment was completed, the 2, 3-DPG levels of the blood were measured. These results are listed in Table 6 below.

TABLE 6

(Measuring method: enzyme method, "2, 3-DPC Test" provided by Boerhinger Mannheim-Yamanouchi, Inc.)
Unit: µmol/gHb     n = 3     average value ± SD

| Fresh blood | Replacement of preserving fluid was made at 0° C. and preserved for 12 weeks | After rejuvenation treatment |
|---|---|---|
| 13 ± 8 | 7 ± 3 | 28 ± 12 |

As confirmed by the data listed in Table 6, it was possible to rejuvenate red blood cells by performing the rejuvenation treatment described above.

As each result mentioned above shows, storage fluid replacement in accordance with the present invention makes it possible to effectively store blood for extended periods of time. Furthermore, the bag arrangement according to the present invention allows for easy handling of the storage bag when carry out operations such as centrifuging, removing the storage bag from storage, placing the storage bag into storage, and the like. Furthermore, as only a relatively small storage space is required for the storage bag according to the present invention, overall operations can be more easily carried out. Moreover, the bag arrangement according to the present invention makes it possible to carry out fluid replacement for several times while sufficiently maintaining sterile conditions inside the storage bag.

The cell storage bag system and cell storage method according to the present invention, as described in detail above, makes it possible to ensure sterile conditions when adding fluid to the storage bag or when collecting fluid from the storage bag by connecting tubes to tubes of the storage bag with a tube connecting apparatus. Moreover, as the storage bag according to the present invention is a single unit bag that can be handled independently from the other bags, handling of the bag and work involving the use of the bag are greatly simplified, and this makes it much easier to prevent misoperations or accidents involving storage bags.

In particular, as the replacement of fluids is carried out within a closed system, it is possible to prevent the occurrence of fluid leakage and contamination caused by microbes entering the system.

Furthermore, as the parameters of the additive fluid, such as the type, composition, density and quantity, may be freely changed, for example, or changing the composition or density of the storage fluid one by one, changing the amount of additive fluid. Further, other types of additive fluid such as fluid for rejuvenating or washing the cells can be added after supply of the preserving fluid and waste thereof. Therefore, it is possible to provide the optimum conditions for storing the cells. As a result, the present invention makes it possible to vastly improve the overall cell storage capabilities of storage bag systems.

Moreover, as the storage bag according to the present invention is separated from other storage containers and is placed into storage by itself, the storage bag does not take up much storage space, and this allows for effective use of storage facilities and thereby lowers the cost of storing the storage bag.

Finally, it should be noted that the present invention is no limited to the embodiments as described above, and that the scope of the present invention will be determined only by the following claims.

What is claimed is:

1. A method of preserving cells in a storage bag using a cell preserving bag system, which system comprises a storage bag which contains preservation fluid containing cells to be preserved, said storage bag including at least one connecting tube having a first end that communicates with said storage bag and a second end that is closed; a reservoir container which contains additive fluid, said reservoir container including a fluid supply tube having a first end that communicates with said reservoir container and a second end that is closed; and a waste fluid container for receiving waste fluid generated in said storage bag, said waste fluid container including a waste fluid tube having a first end that communicates with said waste fluid container and a second end that is closed; wherein the method comprises the steps of:

connecting said connecting tube with said waste fluid tube sterilely using a tube connecting apparatus which can connect two tubes in a sterile manner, and then transferring the waste fluid from said storage bag to said waste fluid container through said connected tubes to collect the waste fluid in said waste fluid container; and connecting said connecting tube with said fluid supply tube sterilely using said tube connecting apparatus, and then transferring the additive fluid contained in said reservoir container to said storage bag, wherein the steps are carried out during the preservation of the cells and repeated a plurality of times, and the additive fluid to be added to said storage bag is selected from the group consisting of a blood preserving fluid, a rejuvenating fluid and a physiological saline solution, wherein in the case in which the additive fluid is a blood preserving fluid, the step of transferring the additive fluid is carried out under a lower preserving temperature of from 0° C. to 4° C., and in the case in which the additive fluid is a rejuvenating fluid, the step of transferring the additive fluid is carried out after raising the temperature of the preservation fluid in the storage bag being preserved under the lower preserving temperature to a predetermined temperature, in which the addition of the rejuvenating fluid is carried out after a plurality of replacement of the blood preserving fluid.

2. The cell preserving method as claimed in claim 1, wherein said predetermined temperature is room temperature or body temperature.

3. The cell preserving method as claimed in claim 1, wherein the preservation fluid is replaced periodically.

4. The cell preserving method as claimed in claim 1, wherein said waste fluid container and said reservoir container connected to said storage bag are separated from each other by sealing a connected portion of the connected tubes therebetween and then cutting the sealed section, respectively.

5. A method of preserving cells in a storage bag using a cell preserving bag system, which system comprises a storage bag which contains preservation fluid containing cells to be preserved, said storage bag including a first connecting tube having a first end that is closed and a second end that communicates with said storage bag and a second connecting tube having a first end that is closed and a second end that communicates with said storage bag; a reservoir container which contains additive fluid, said reservoir container including a fluid supply tube having a first end that communicates with said reservoir container and a second end that is closed; and a waste fluid container for receiving waste fluid generated in said storage bag, said waste fluid container including a waste fluid tube having a first end that communicates with said waste fluid container and a second end that is closed; wherein the method comprises the steps of:

(a) separating the preservation fluid contained in the storage bag into two layers including an upper layer containing the waste fluid and a lower layer containing the cells;

(b) connecting the first end of said second connecting tube with the second end of said waste fluid tube sterilely using a tube connecting apparatus which can connect two tubes in a sterile manner;

(c) transferring the waste fluid in the upper layer in said storage bag to said waste fluid container through the connected tubes to collect the waste fluid in said waste fluid container;

(d) separating the waste fluid container from the storage bag by sealing a connected portion of the connected tubes and then cutting the portion;

(e) connecting the first end of said first connecting tube with the second end of said fluid supply tube sterilely using said tube connecting apparatus;

(f) transferring the additive fluid contained in said reservoir container to said storage bag through said connected tubes; and (g) separating said reservoir container from said storage bag by sealing a connected portion ot the connected tubes and then cutting the portion, wherein the steps (a) to (g) are carried out during preservation of the cells and repeated a plurality of times, and the additive fluid to be added to said storage bag is selected from the group consisting of a blood preserving fluid, a rejuvenating fluid and a physiological saline solution, wherein in the case in which the additive fluid is a blood preserving fluid, the steps (a) to (g) are carried out under a lower preserving temperature of from 0° C. to 4° C., and in the case in which the additive fluid is a rejuvenating fluid, at least step (f) is carried out after raising the temperature of the preservation fluid in the storage bag being preserved under the lower preserving temperature to a predetermined temperature, in which the addition of the rejuvenating fluid is carried out after a plurality of replacements of the blood preserving fluid.

6. The cell preserving method as claimed in claim 5, wherein in the case in which the additive fluid is a rejuvenating fluid, said steps (a) to (g) are carried out after raising the temperature of the preservation fluid in the storage bag, the preservation fluid being preserved under the lower preserving temperature to a predetermined temperature.

7. The cell preserving method as claimed in claim 6, wherein said predetermined temperature is room temperature or body temperature.

8. The cell preserving method as claimed in claim 5, further comprising the step of preserving the storage bag to which the additive fluid has been added, under the lower preserving temperature.

9. The cell preserving method as claimed in claim 5, wherein in each of the steps (d) and (g) the sealing and cutting of the connected tubes is carried out by sealing a midsection of said connected tubes which are connected by said tube connecting apparatus and then cutting the sealed section to form separate sealed end portions.

10. The cell preserving method as claimed in claim 5, wherein said step (b) is carried out before said step (a).

11. The cell preserving method as claimed in claim 5, wherein said step (d) is carried out together with said step (g) after the step (f).

12. The cell preserving method as claimed in claim 5, wherein said step (a) is carried out by centrifugal separation.

13. The cell preserving method as claimed in claim 5, wherein the preservation fluid is replaced periodically.

14. A method of preserving cells in a storage bag using a cell preserving bag system, which system comprises a storage bag which contains the preservation fluid containing cells to be preserved, said storage bag including a connecting tube having a first end that communicates with said storage bag and a second end that is closed; a reservoir container which contains additive fluid, said reservoir container including a fluid supply tube having a first end that communicates with said reservoir container and a second end; a waste fluid container for receiving waste fluid generated in said storage bag, said waste fluid container including a waste fluid tube having a first end that communicates with said waste fluid container and a second end; and a connection tube having a first end that is connected to both the second ends of said fluid supply tube and said waste fluid tube and a second end that is closed; wherein the method comprises the steps of:

(a) separating the preservation fluid containing the cells contained in the storage bag into two layers including upper layer containing the waste fluid and lower layer containing the cells;

(b) connecting the second end of said connecting tube with the second end of said connection tube sterilely using a tube connecting apparatus which can connect two tubes in a sterile manner;

(c) blocking an inner fluid path of said fluid supply tube, thereby transferring the waste fluid contained in the upper layer in said storage bag to said waste fluid container through connecting tube, said connection tube and said waste fluid tube to collect the waste fluid in said waste fluid container;

(d) blocking an inner fluid path of said waste fluid tube and opening the blocked inner fluid path of said fluid supply tube, thereby transferring the additive fluid in said reservoir container to said storage bag through said fluid supply tube, said connection tube and said connecting tube; and (e) separating said waste fluid container and said reservoir container from said storage bag by sealing a connected portion of the connected tubes and then cutting the portion, wherein steps (a) to (e) are carried out during preservation of the cells and repeated a plurality of times, and the additive fluid to be added to said storage bag is selected from the group consisting of a blood preserving fluid, a rejuvenating fluid and a physiological saline solution, wherein in the case in which the additive fluid is a blood preserving fluid, the steps (a) to (e) are carried out under a lower preserving temperature of from 0° C. to 4° C., and in the case in which the additive fluid is a rejuvenating fluid, at least step (d) is carried out after raising the temperature of the preservation fluid in the storage bag being preserved under the lower preserving temperature to a predetermined temperature, in which the addition of the rejuvenating fluid is carried out after a plurality of replacements of the blood preserving fluid.

15. The cell preserving method as claimed in claim 14, wherein in the case in which the additive fluid is the rejuvenating fluid, said steps (a) to (e) are carried out after raising the temperature of the preservation fluid in the storage bag being preserved under said lower preserving temperature to a predetermined temperature.

16. The cell preserving method as claimed in claim 15, wherein said predetermined temperature is room temperature or body temperature.

17. The cell preserving method as claimed in claim 14, further comprising the step of preserving the storage bag to which the additive fluid has been added, under the lower preserving temperature.

18. The cell preserving method as claimed in claim 14, wherein in the step (e) the sealing and cutting of the connected tubes is carried out by sealing a midsection of said connected tubes which are connected by said tube connecting apparatus and then cutting the sealed section to form separate sealed end portions.

19. The cell preserving method as claimed in claim 14, wherein said step (a) is carried out by a centrifugal separation.

20. The cell preserving method as claimed in claim 14, wherein the preservation fluid is replaced periodically.

21. The cell preserving method as claimed in claim 14, further comprising the step of supplying washing fluid contained in a fluid supply bag to said storage bag for washing the cells after discharging the waste fluid in said storage bag.

22. The cell preserving method as claimed in claim 21, wherein said fluid supply bag is provided with a waste fluid bag for receiving the washing fluid used for the washing.

* * * * *